United States Patent [19]

Grassi

[11] Patent Number: 4,655,773
[45] Date of Patent: Apr. 7, 1987

[54] BICUSPID VALVE PROSTHESIS FOR AN AURICULO-VENTRICULAR CARDIAC APERTURE

[75] Inventor: Gino Grassi, Sesto Fiorentino, Italy

[73] Assignee: GE. SV. IN. S.r.l., Italy

[21] Appl. No.: 746,970

[22] Filed: Jun. 20, 1985

[30] Foreign Application Priority Data

Sep. 21, 1984 [IT] Italy ................ 3578 A/84

[51] Int. Cl.⁴ ............................. A61F 2/24
[52] U.S. Cl. ..................................... 623/2
[58] Field of Search ............... 623/900, 1.4, 2

[56] References Cited

U.S. PATENT DOCUMENTS 3,739,402  6/1973  Cooley et al. ............. 623/2
4,340,977  7/1982  Brownlee et al. ......... 623/900

Primary Examiner—Richard J. Apley
Assistant Examiner—James Prizant
Attorney, Agent, or Firm—Darby & Darby

[57] ABSTRACT

The disclosed prosthesis for replacement of the bicuspid or mitral valve in the left auriculo-ventricular aperture, or of the tricuspid valve in the right auriculo-ventricular aperture, is fitted to a semi-rigid ellipsoidal and reniform support which imitates the biological shape of the original organ. The moving part of the valve is fashioned from a single piece of biological, bio-compatible or polymeric material, and fabricated such that the sub-valve section is supported by two "suspenders" in order to ensure a singularly biological type of operation, with no drop in pressure incurred during the opening movement, and with minimal regurgitation during the closing movement.

4 Claims, 8 Drawing Figures

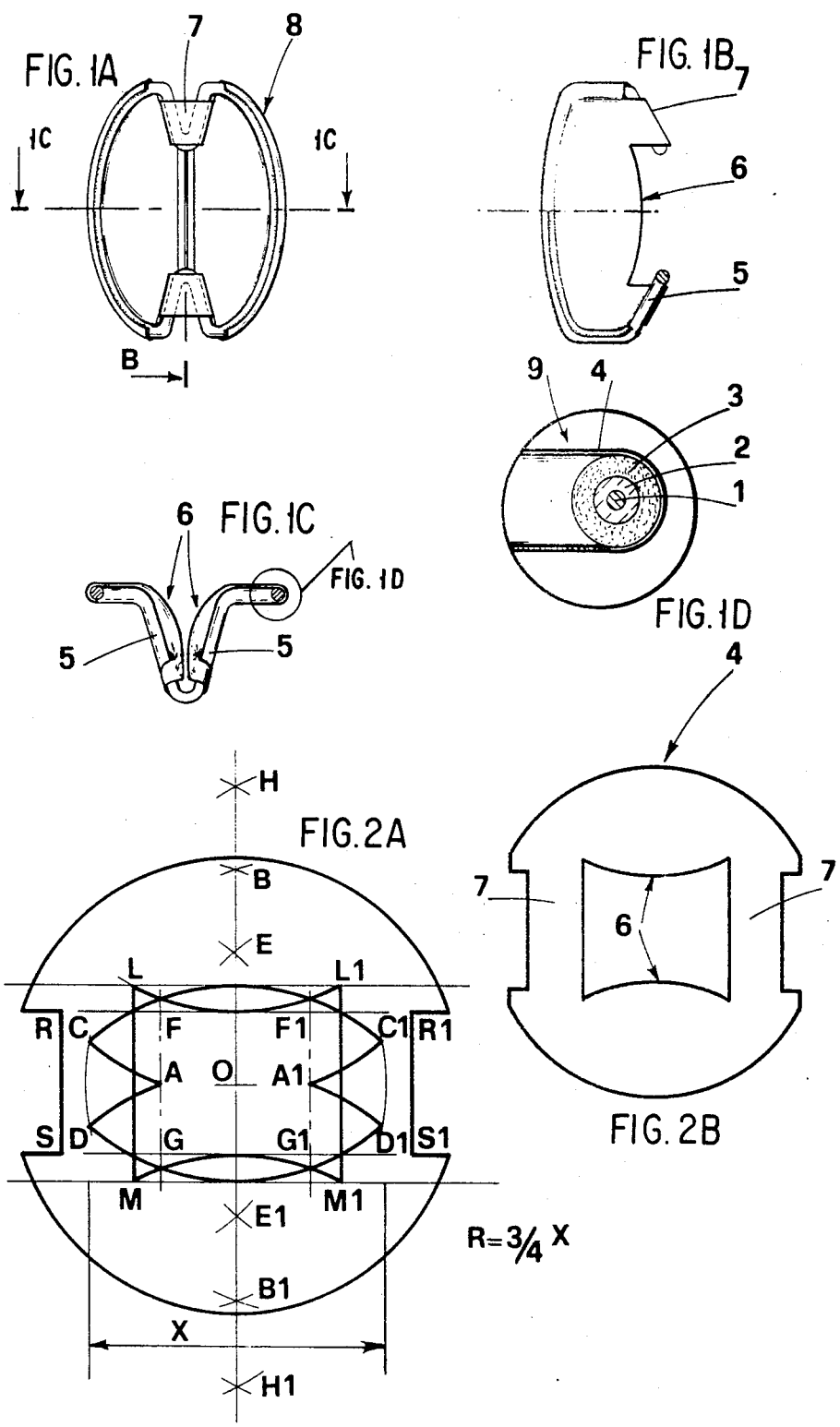

BICUSPID VALVE PROSTHESIS FOR AN AURICULO-VENTRICULAR CARDIAC APERTURE

BACKGROUND OF THE INVENTION

The inadequacy of currently-available types of biological prosthesis used for the replacement of mitral and tricuspid valves is well known, and stems from two fundamental drawbacks.

The first such drawback, relating to tissue, is the lack of long-term reliability; the second, relating to shape, is lack of appropriate prosthetic geometry.

Recently-developed techniques in the fixation of biological materials and the prevention of calcification are such as ought to prolong the average life of valve prostheses. Attempts have been made to overcome the second drawback by embodying biological and mechanical valves having in common the feature of a substantially elliptical annulus.

Such prostheses offer certain advantages over standard commercially-available types, namely: (1) better adaptation of the prosthetic annulus to the anatomical annulus; (2) reduced contact with the ventricle walls and with the left ventricular tract when opening, or with the septum and right auriculoventricular bundle (His's bundle) when closing.

The objection generally voiced against biological prostheses of the bicuspid type is that they tend to induce stenosis by reason of the geometry of the cusps themselves, notwithstanding the mitigating feature of a non-circular support medium, or 'stent' so-called.

Stenosis is avoided by separating and spreading apart the cusps at the commissural ends, and inhibiting reflexive movement of these two areas by means of a sub-valvular apparatus.

OBJECT AND SUMMARY OF THE INVENTION

It is the object of the invention disclosed herein to embody a new type of biological bicuspid prosthesis fitted to an ellipsoidal, or reniform two-pronged flexible stent.

The material employed in fabricating such a prosthesis may be either biological or synthetic, say, glutaraldehyde-treated bovine pericardium in the first instance, and fabric woven from polymers in the second (Dacron or other similar type), and is cut in a single piece for fitting to the stent.

A special feature referred to hereinafter as a "suspender" adopted for the sub-valvular section permits of deriving a favorable operating characteristic from the prosthesis, whereby the two cusps are spread apart during the opening movement with no drop in pressure, and minimal regurgitation is occasioned during the closing movement (2 to 3% of flow capacity).

BRIEF DESCRIPTION OF THE DRAWINGS

The above features will become more apparent from the description of a preferred embodiment of the invention given by way of example with reference to the accompanying drawings in which:

FIG. 1A is a plan view of the bicuspid valve prosthesis according to the present invention;

FIG. 1B is a section view of the bicuspid valve prosthesis taken along line 1B of FIG. 1A;

FIG. 1C is a cross-section view of the bicuspid valve prosthesis taken along line 1C of FIG. 1A;

FIG. 1D shows in an enlarged scale a particular of the prosthesis shown in FIG. 1A;

FIG. 2A is a diagrammatic view of the prosthesis which shows the constructive ratios between the size of the stent and the size of the moving valve part;

FIG. 2B is a plan view of the moving valve part;

DESCRIPTION OF THE PREFERRED EMBODIMENT

Figure 3:
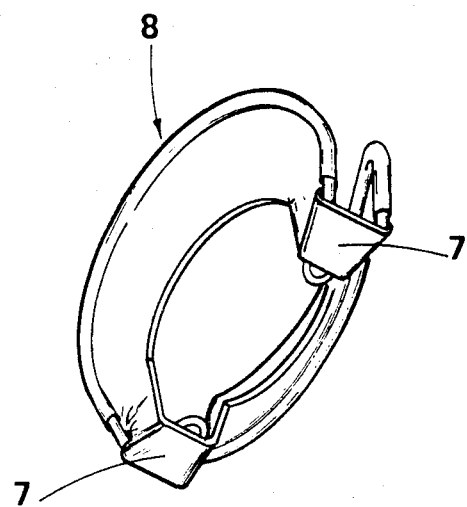
FIG. 3 is a perspective view of the bicuspid valve prosthesis in the opening position.

The valve prosthesis disclosed essentially comprises two parts: the stent, or support medium, and the moving valve part.

The skeleton framework of the stent 1 is in a semi-rigid material which may be metal or plastic (but which must be bio-compatible) shaped in such a way as to create a basic loop having a substantially ellipsoidal or reniform appearance the ends of which depart perpendicularly from the ellipsoid's greater diameter to form two respective prongs 5 (FIG. 1B).

Clearly, the embodiment may vary according to whether the valve prosthesis is intended for right auriculo-ventricular application (tricuspid) or for left (mitral).

The prongs 5 are bent inward at approximately halfway along their length through a preferred angle of 75° though this inclination admits of variation. What is more, the length of the two prongs need not of necessity be identical.

The stent 1 must be a semi-rigid embodiment in view of the mechanical stresses acting upon it, especially those affecting the annulus, which are caused principally by the action of cardiac muscles.

Whether metallic or plastic, the skeleton framework of the stent will be clad in its entirety with a flexible sheath 2 such as Silastic or Dacron velour, and this sheath, in its turn, covered with a woven polymer fabric 3 (Dacron or similar). Both of these coverings must be bio-compatible.

A second loop is applied externally to the basic reniform loop thus embodied, so as to provide an anchor for the surgeon's suture when fitting the prosthesis to the annulus of the patient. The loop (or garter) in question will be in a woven polymer fabric, integrated perhaps by silicon foam, and is not illustrated, being identical to the type used with conventional prosthesis and therefore known to one having skill in the art.

The moving valve part of the prosthesis is embodied in a single piece 4 of material which may be either biological, such as bovine pericardium treated, say, with glutaraldehyde, or synthetic and bio-compatible (a polymer such as Dacron).

The single piece 4 of material is contoured and cut out at the center as in FIG. 2B, then sutured to the support medium 9 with non-reabsorbable thread so as to provide the moving part of the valve.

Detailed measurements of a stent and moving valve part according to the invention may be calculated from a single pilot diagram adapted to the size of the prosthesis it is sought to embody. FIG. 24 of the drawings shows such a diagram for ellipsoidal prostheses.

The description and illustrations relate to an nonlimiting example of the procedure for arrival both at the basic shape of the ellipsoidal stent and the shape to be cut from the sheet of bio-compatible or biological material selected for the moving valve part.

The ellipsoidal valve to be embodied has an overall axial length (prong-to-prong) denoted X a circle having $R = \frac{3}{4}X$ is marked out on the sheet;

two points A and A1 are marked out on a given diameter at $\frac{1}{3}R$ from center 0, symmetrical thereto;

with compasses set at radius R, arcs are marked out from centers A and A1 so as to intersect at points B and B1, which coincide with and lie symmetrically on a diameter normal to that initially selected;

with compasses still set at radius R, two arcs are marked out so as that each end intersects those circles having radius R centered on A and A1, thus obtaining points C, C1 and D, D1 which determine the greater diametral dimension of the stent;

with compasses at radius R, centering on these four points, arcs are marked out so as to obtain points E and E1, from where further arcs are drawn between D and D1 and C and C1, respectively, in order to establish the perimetral outline of the ellipsoidal stent.

The opening which must be cut from the piece of material so as to fashion the cusps and the suspenders is marked out as follows:

points F, F1 and G, G1 are found by intersecting arcs C-C1 and D-D1 with two parallel lines passing through points A and A1 normal to the diameter initially selected;

with compasses set at radius R, centering on F, F1, and G, G1, arcs are marked out such as to intersect at points H and H1, from where respective arcs are then drawn to pass through F-F1 and G-G1;

lines are drawn tangential to the two arcs centered on E, E1 establishing the outline of the sent, and parallel to the diameter initially selected;

the points at which these two parallel lines intersect with the arcs centered on H and H1 provide the four vertexes L, L1 and M, M1 of the opening to be cut out, which is drawn in bold line.

The basic outline of the stent (C-C1, D-D1) and the projection of the prongs (C-A-D, C1-A1-D1) are likewise illustrated in bold line.

The prongs are disposed perpendicular with respect to C-D and C1-D1, and will be approximately $\frac{1}{3}R$ in length, though not necessarily identical in length.

The above procedure permits of fabricating a quasi-ellipsoidal valve, embodied according to the invention, accomplished in simple fashion and having markedly physiological characteristics.

The piece of material cut out in the manner described will be sutured to the stent as in FIG. 1 utilizing non-absorbable thread.

Dimensions for the suspenders are established as follows:

lines are drawn parallel to the diameter initially selected and tangential to arcs L-L1 and M-M1;

the points at which these lines intersect with the arcs passing through C, C1 and D, D1 provide four references R, R1 and S, S1;

the parallel segments lying between R-S and L-M and between R1-S1 and L1-M1 thus provide two suspenders according to the invention.

The outer edge of each suspender is embodied shorter so as to afford a more stable anchorage to the prongs.

The moving valve part of the prosthesis has two principal sections which operate simultaneously during the opening and closing movements, namely: the two cusps 6, and the sub-valvular apparatus, or suspenders 7 supporting them.

A prosthesis of the auriculo-ventricular type disclosed is implanted in such a way that the basic loop 8 is sutured to the annulus of the patient's heart with the moving valve part directed downwards into the ventricle.

The prosthesis opens (see FIG. 3) in response to the auriculo-ventricular flow of blood into the ventricle; the two cusps separate, spreading apart and downwards in relation to the stent, toward the ventricle.

Full opening of the valve is brought about with simultaneous separation and spreading apart of the cusps, and of the suspenders connected thereto, which in this position tend to open out within the same plane as the cusps.

Figure 4:
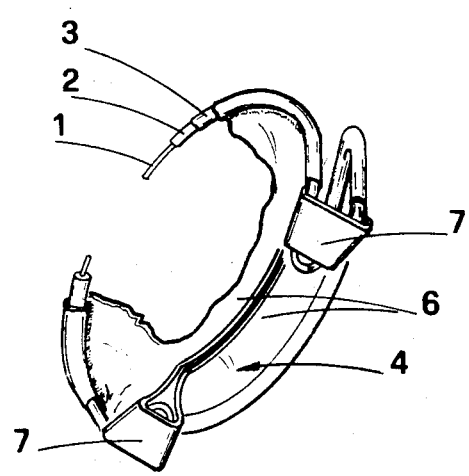
FIG. 4 is a perspective view of the bicuspid valve prosthesis in the closed position.

Subsequent contraction of the ventricle will close the prosthesis as in FIG. 4, and during such contraction, or systole, the cusps 6 are drawn together and upwards toward the annulus, assuming a partially collabent posture under the pressure of blood.

The valve's fully-closed position is arrived at with the cusps and the suspenders being drawn together in such a way that the suspenders are held taut by the prongs so as to prevent the cusps from reflexing, that is, turning inside-out and through the loop defined by the stent. The suspenders are in fact held in position by the projecting parts of the two prongs 5.

It will be observed that, unlike conventional types of mitral or tricuspid prostheses currently marketed, a valve according to the invention has no commissural points, i.e., when the cusps are spread apart, they are separated completely. Such a feature constitutes a marked advantage since calcification, which occurs most of all in commissural areas, can be kept to a minimum.

What is claimed:

1. A bicuspid valve prosthesis for an auriculoventricular cardiac aperture comprising:
    a bio-compatible material stent having a substantially ellipsoidal basic loop shape and two prongs which depart perpendicularly from a greater diameter of the ellipsoidal basic loop, said prongs being sloped inwardly of the stent; and
    a moving valve part formed from a single piece of biocompatible material, the moving valve part having a cut out formed in the center thereof and being sutured to the stent, said single piece including two cusps adapted to operate simultaneously for opening and closing movements of the valve, and suspenders mounted on the prongs for supporting the cusps.

2. The bicuspid valve prosthesis as in claim 1 wherein the moving valve part is formed from biological material.

3. The bicuspid valve prosthesis as in claim 1 wherein the moving valve part is formed from a polymeric material.

4. The bicuspid valve prosthesis as in claim 1 which further comprises:
    a flexible sheath clad on the stent; and
    a woven polymer fabric clad on the flexible sheath for suturing the moving valve part to the stent.

* * * * *